United States Patent
Tran (10) Patent No.: US 7,175,986 B2
(45) Date of Patent: Feb. 13, 2007

(54) METHODS AND REAGENTS FOR DIFFERENTIAL PROTEOMIC ANALYSIS

(75) Inventor: Nathaniel Tue Tran, Irvine, CA (US)

(73) Assignee: Proteomyx Inc., Temecula, CA (US)

( * ) Notice: Subject to any disclaimer, the term of this patent is extended or adjusted under 35 U.S.C. 154(b) by 20 days.

(21) Appl. No.: 10/835,027

(22) Filed: Apr. 28, 2004

(65) Prior Publication Data

US 2005/0074794 A1 Apr. 7, 2005

Related U.S. Application Data (63) Continuation-in-part of application No. 10/680,277, filed on Oct. 7, 2003, now Pat. No. 7,029,855.

(51) Int. Cl.
 *C12Q 1/68* (2006.01)
 *G01N 33/53* (2006.01)

(52) U.S. Cl. .......................................... 435/6; 435/7.1

(58) Field of Classification Search ............... 435/6, 435/7.1
 See application file for complete search history.

(56) References Cited

U.S. PATENT DOCUMENTS

| | | | |
|---|---|---|---|
| 4,886,761 A * | 12/1989 | Gustafson et al. | 436/518 |
| 6,379,970 B1 * | 4/2002 | Liebler et al. | 436/86 |
| 2002/0076817 A1 * | 6/2002 | Figeys et al. | 436/6 |
| 2003/0013126 A1 * | 1/2003 | Singh et al. | 435/7.1 |

* cited by examiner

*Primary Examiner*—Ethan Whisenant (57) ABSTRACT

Methods and reagents for labeling molecules of interest in a plurality of samples, and then combining and selecting labeled molecules away from unlabeled molecules for use in simultaneous co-assaying analysis. The reagents comprise labeling means of distinguishable radioactive isotopes which remain with the labeled molecules. Additionally, the reagents also comprise selection means which can be affinity tags, beads, or immobilized surface which may remain or be cleaved off through cleavable linkers. A set of labeling reagent can be used to label a plurality of samples, combine them before or after selecting/enriching for labeled molecules and co-assay together for reliable comparison. This invention has many applications in comparing and panning for differentially abundant molecules or differential modification of molecules for proteomics, glycomics, phospho-proteomics, metabolomics, epi-genomics . . . studies.

17 Claims, 2 Drawing Sheets

METHODS AND REAGENTS FOR DIFFERENTIAL PROTEOMIC ANALYSIS

CROSS-REFERENCE TO RELATED APPLICATIONS

This application is a continuation-in-part of U.S. patent application Ser. No. 10/680,277 filed Oct. 12, 2003 now U.S. Pat. No. 7,029,855. This application also claims priority of international patent application serial number PCT/US 04/02442 file Jan. 28, 2004. The content of both these patent applications are incorporated herein in their entirety as reference.

FIELD OF THE INVENTION

This invention relates to a method for labeling proteins and other molecules in different samples and then combining these samples for simultaneous co-analysis for more reliable qualitative and quantitative comparison between the samples.

BACKGROUND OF THE INVENTION

Many biological processes in living cells are controlled by alterations in the levels or states of certain key proteins and metabolites. Measuring the levels of the various proteins that affect (or are affected by) the process is therefore important for gaining an understanding of the biological process. For example, a given hormone may, through a signaling cascade, activate certain key transcription factors which in turn induce the expression of a number of proteins with distinct activities. Comparison of the levels of the proteins in the cell prior to and after induction can indicate which gene products are being up regulated and/or down regulated by the action of the hormone. As a second example, comparison of the total complement of proteins from an organism (the proteome) prior to and after infection with a pathogen can show which proteins are up and/or down regulated by the infection. Such an analysis can provide important information about the mechanism by which the pathogen subverts its host cell, thereby aiding in the development of therapeutic drug strategies. Similarly, comparison of some or all of the proteins of the proteome before and after treatment with a drug can indicate the mechanism of action of the drug, as well as its potential effectiveness and toxicity. Yet another example, measurement of the state of phosphorylation of protein members of an intracellular cascade involved in turning on and off a given biological process can provide information about the control of the signaling pathway.

A facile method for accurately comparing the levels of proteins and other cellular components and biological materials as a function of time or as the result of particular treatment, such as a hormone, a drug, or a virus, as mentioned above, or an environmental stimulus, such as a temperature change, is needed. It is also necessary to assay these protein levels with high degree of accuracy because small changes in the levels of certain key proteins may, through a complex cascade of molecular events, produce large changes in the biological system.

Current proteomic analysis methods used different means of separations to profile proteins with different properties for comparison. A two dimensional gel can be used to separate proteins by their isoelectric points and sizes so that many proteins can be examined. High degree of reproducibility between samples is required to make meaningful comparison thus evolve multiplexing co-analysis methods. Proteins can be labeled with different fluorescent dyes such as Cy2, Cy3, or Cy5 and then combined together to be co-separate on the same 2-D gel simultaneously. The dyes are engineered so that their contribution in mass and charge to the proteins they label are the same or almost the same while having different absorption and emission spectra. As a result, after analysis the quantity of proteins originated from one sample can be determined and compared with other samples. Overall, enabling coding of samples so they can be combined for analysis and then decode at the end for quantitative comparison yield much more reliable analysis than separate side-by-side or sequential analyses of one sample at a time.

Another recent advance uses heavy isotope to label a protein sample to be combined with a non-labeled (normal isotope labeled) protein sample. The labeling can be done by heavy isotopes incorporation if the protein is undergoing synthesis by $^{15}N$, $^{13}C$, $^{18}O$ . . . etc. There are also labeling reagents that label proteins that are already synthesized for analysis. One such reagent is called Isotope-Coded Affinity Tag (ICAT) reagent described in Aebersold et al. WO01/94935; WO03/102220; US2002/0168644; U.S. Pat. No. 6,670,194; WO03/102018; WO00/11208. This type of reagent not only allows labeling of proteins through specific functional groups such as amines, thio . . . etc. but also allows affinity selection of labeled proteins away from unlabeled molecules. A pair of ICAT reagent differs only in that one carry heavy isotope and the other carry normal isotope.

Similar to isotope labeling, using ICAT reagent to label two samples of proteins, one can then combine the two samples for co-analysis by any means that separate the different proteins apart so that they can be quantified and characterized individually. The interest here is to compare the quantity or level of abundance, thus mass spectrometry is used to make the determination. Upon analysis by mass spectrometry, proteins or peptides originated from different samples can be distinguished by their shifted mass peak. Then the peak height of one can be compared against that of the other thus enable quantitative comparison.

The majority of proteins don't increase or decrease in their expression levels due to a stimulus. The above analysis requires that mass spectrometry be used to analyze all proteins in both samples to spot just a few that are differentially abundant. Despite recent advances in instrumentation and supported software, mass spectrometry and especially analyses of the mass spectra themselves is still a very expensive and time consuming process. If just 1% of proteins between two samples are differentially abundant, then 99% of mass spectrometry analyses are redundant. As a result, there is a need for more efficient methods to quantitatively compare proteins between samples.

SUMMARY OF THE INVENTION

Briefly described, this invention teaches methods for labeling at least two samples of test molecules so that they can be distinguished even though they will behave the same when they are combined for simultaneous co-analysis. The methods use a pair or a trio of chemically similar labeling reagents containing different radioactive isotopes. In addition to labeling the molecules of interest, these reagents also provide a means to select labeled molecules away from unlabeled molecules thus further improve the analysis. Additionally, the relative abundance of all molecules can be determined after the mixture is fractionated by a simple step of selective quantification of different radioactive isotopes.

Such quantification can be performed by rapid scintillation counting in stead of the time-consuming mass spectrometry analysis.

This invention teaches methods involve the use of these reagents for the rapid, and quantitative analysis and comparison of molecules especially proteins between a plurality of samples. The analytical method can be used for qualitative and particularly for quantitative analysis of global protein expression profiles in cells, fluids and tissues, i.e. the quantitative analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-directed mutation, gene knockouts) of the cell, tissue or organism from which the sample originated. The proteins identified in such a screen can function as markers for the changed state. For example, comparisons of protein expression profiles of normal and malignant cells can result in the identification of proteins whose presence or absence, increase or decrease in abundance is characteristic of the malignancy.

The novel method employs reactive reagents that will covalently modify and allow for the selective isolation of labeled molecules of interest (after labeling) away from unlabeled molecules. Such selection enriches the pool of molecules to be analyzed. Such selection also helps eliminate many other types of molecules that may inadvertently interfere with any further analyses. The labeling reagent contains a reactive group that can react generally or specifically toward a chemical functional groups. Such a group can covalently modify amines, ketones, thio groups on proteins, hydroxyl groups in proteins, lipid and carbohydrates depending on the types of molecules needed to be labeled.

One type of labeling reagent comprises of a biotin or biotin derivative such as imino-biotin containing either Tritium ($^3$H), Carbon-14 ($^{14}$C), or Sulfur-35 ($^{35}$S). The biotin provides a simple way for affinity purification by binding to immobilized avidin or strepavidin. The radioactive atoms provide an easy way to detect and quantify the quantity of labeled molecules. The different radioactive isotopes allow easy and rapid selective quantification of each isotope in a mixture for quantitative comparison of similar molecules especially when they are mixed together for simultaneous multiplexing analysis. The use of radioactive isotopes as elemental replacement in labeling compounds makes it possible to have chemically identical labeling reagents that are physically distinguishable. While the identical pair or trio is preferred, those that are sufficiently similar can also be used if necessary.

Another type of labeling reagent comprises of an immobilizer connected to a cleavable linkage which is connected to a reactive group. Molecules getting labeled are immobilized so that unlabeled molecules can be washed away. Then labeled molecules can be uncoupled or cleaved off at the cleavable linkage with the useful part of the label still remaining. The immobilizer can be a bead or a solid surface such as that in a reaction vessel. Some can also have activated surface so that the rest of the label can be coupled to it when needed and then uncoupled after labeling and selection.

The method of this invention can be applied to determine the relative quantities of one or more proteins in two or more protein samples, the proteins in each sample are reacted with selection reagents which are substantially chemically identical but differentially isotopically labeled. The samples are combined and processed as one. For some analyses, bulky proteins need to be hydrolyzed into more manageable fragments to be labeled efficiently. The relative quantity of each tagged peptide which reflects the relative quantity of the protein from which the peptide originates is determined by the measurement of the respective isotope's radiation. Such measurement can be done by simple scintillation counting or similar methods for quantifying radiation.

One object of the invention is to provide a method for labeling molecules of interest, purifying labeled molecules away from unlabeled molecules for better analysis. The method uses the labeling reagents containing a pair of different radioactive isotopes. Affinity tags or immobilizers enable rapid affinity purification. The radioactive isotopes enable rapid detection and quantitative comparison especially when at least two samples are multiplexed together having similar molecules labeled with different isotopes.

In one embodiment of the present invention, a method for comparing the relative abundance of a protein of interest in multiple samples of biological matter is disclosed, wherein one of the samples has been modulated by exposure to a treatment, such as a bacteria, virus, drug or hormone, or a stimulus, such as a chemical or environmental stimulus. A first sample of the biological matter is labeled with a group containing one radioactive isotope such as $^3$H. While a second sample of the biological matter is labeled by a similar group containing another radioactive isotope such as $^{14}$C. The two samples got labeled equally because the labeling reagent can be made chemically identical using different isotopes of the same elements. Both samples are then combined for co-analysis so that molecules in both samples are treated equally making them ideal for comparison. The molecules can be separated into groups so that they can be easily compared quantitatively.

In another embodiment, a distinguishable quality of molecules of interest can be quantitatively compared in two samples. One such quality is the post-translational modification of proteins such as phosphorylation and glycosylation. Similar approaches as described above can be used in conjunction with separation methods that can separate modified molecules from unmodified ones. Alternatively, labeling reagents can be made to selectively label just one form of the proteins. The modifications can be the same type of modification that the proteins got such as phosphorylation or glycosylation but with radioactive isotopes and possibly selection tags.

DETAIL DESCRIPTION OF THE INVENTION

Methodology—

Figure 1:
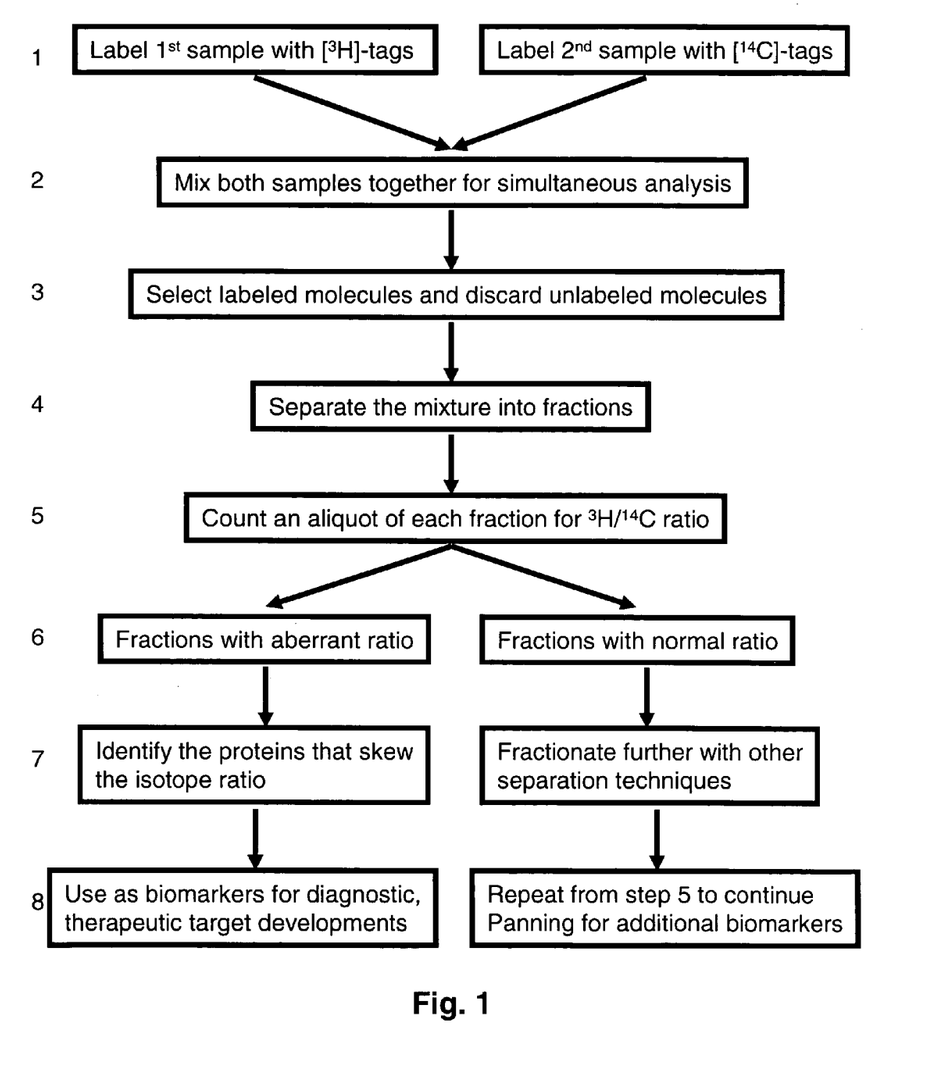
FIG. 1 is a flowchart for the differential proteomic panning process utilizing this invention.
Figure 2:
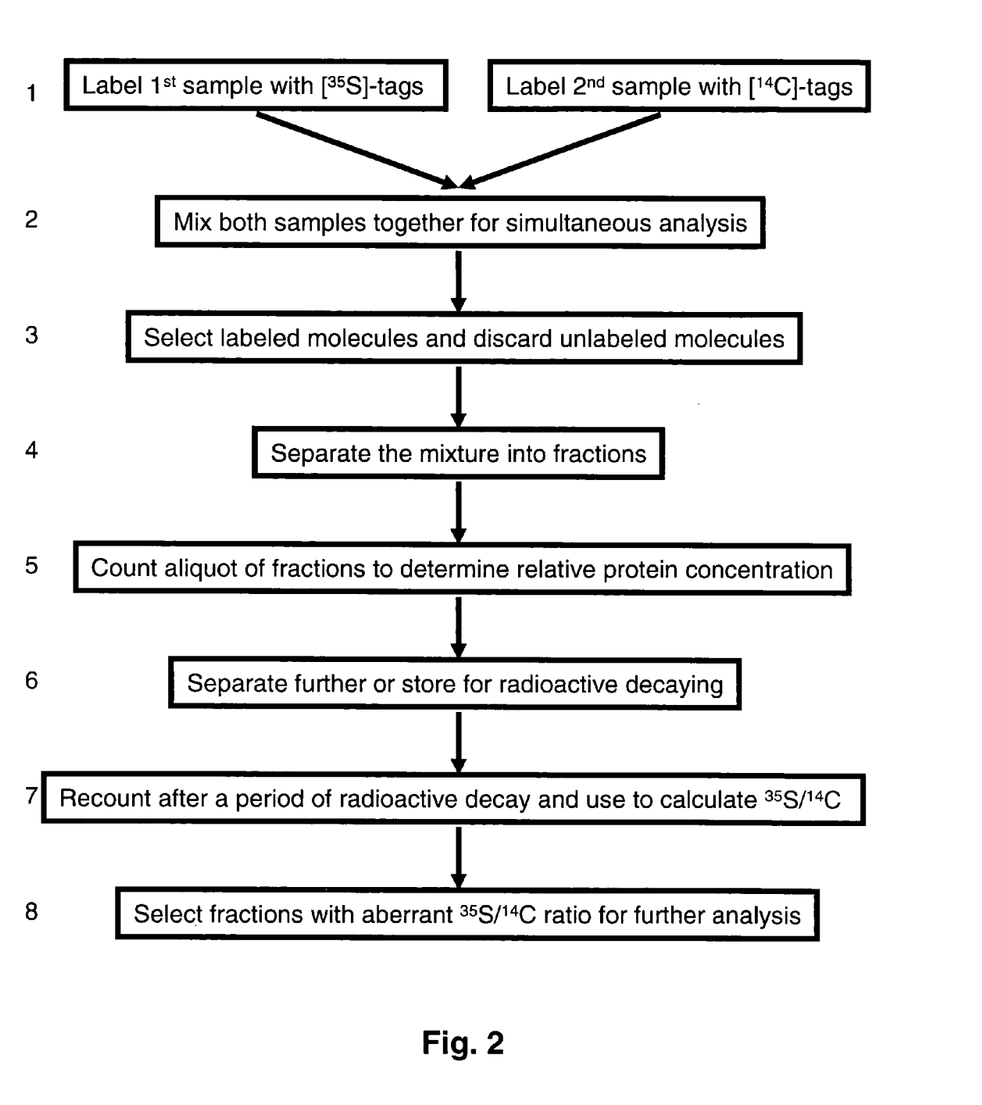
FIG. 2 is a flowchart for an alternative differential proteomic panning process

The methods of this invention employ reactive reagents linked to an immobilizer or an affinity tag to enable selection of reacted molecules from non-reacted molecules. The affinity tag can be covalently attached to a reactive group directly or through an optional spacer and or cleavable linker. An immobilizer needs to be linked to a reactive group through a linker to provide sufficient spacing for the reaction to take place. In addition, if the reacted molecules of interest need to be released from the immobilizer for further experimentation, then the linker should be cleavable. Reactive groups can be made to target specific functional groups such as =O, —OH, —NH$_3$, —COOH, —SH, —PO$_4$, NO$_3$, SO$_4$, etc. depending on the need to label which type of molecules. The affinity tag, the reactive group or the linker can be labeled with different radioactive isotopes such as $^3$H, $^{14}$C, $^{35}$S, $^{32}$P, $^{33}$P etc . . . by replacing one of the atom within these molecules with its radioactive isotope equivalent. For example a trio of reagents containing biotin tag can have identical chemical structure with one label with $^3$H, while another one labeled with $^{14}$C and yet another one labeled with $^{35}$S. Molecules labeled with these tags can be combined for simultaneous co-analysis and then the signal from isotopes such as $^3$H or $^{14}$C or $^{35}$S can be differentially quantified due to their difference in radiation energy or half-life. Radiation from $^{14}$C is stronger thus generating a broader scintillation spectrum compare to radiation from $^3$H. Stronger radiation also have more penetrating power, thus differential screening can also allow differential quantification., If $^{14}$C and $^{35}$S tags are used then the signal from each isotope can be determined by comparing signals read before and after a define period of radioactive decay. The half-life of $^{14}$C is 5730 years thus signals from $^{14}$C will remain almost the same while signals from $^{35}$S will be reduced by half after 87.2 days.

The method can be applied to study differentially abundant molecules between samples. It can also be used to quantify the amount of one or more molecules in a sample using known amount of the same molecules in another sample or standard. Additional variations allow differential quantification and comparison of a quality of different molecules between samples. Good examples are the degree of post-translational modification done to proteins, and methylation done to DNA . . . etc.

Affinity Tags—

Suitable affinity tags are those that bind selectively with high affinity to a capturing agent. This binding should remain intact after extensive and multiple washings with a variety of solutions to remove non-specifically bound components. The affinity tag binds minimally or preferably not at all to components in the assay system, and does not significantly bind to surfaces of reaction vessels. Any non-specific interaction of the affinity tags with other components or surfaces should be disrupted by multiple washes that leave the interaction between the capturing agents and affinity groups intact. Further, it should be possible to disrupt the interaction of the affinity tag and the capturing agent to release the molecules of interest especially when a cleavable linkage is not used. Take biotin as an example can be captured by avidin or strepavidin and then disrupted by chaotropic solution such as 6M guanidium or 6M urea. Imino-biotin can perform the same functions and can be disrupted gently by lowering the pH. Various affinity tags/capturing reagents pairs can be used depending on the specific needs and the types of experiments to be performed.

Another requirement for the affinity tag is that it is relatively inert and preferably soluble in the same liquid used for the sample of test molecules to be labeled. The entire labeling reagents should be able to access molecules of interest and react with them. Optionally, other requirements are compatibility with methods of analysis used down stream depending on the intended use.

Examples of affinity tag and capturing reagent pairs include: d-biotin or structurally modified biotin-based reagents such as d-iminobiotin, which bind to proteins of the avidin/strepavidin family; oligo histidines which bind to chelated transition metals such as nickel and cobalt; ssDNA oligos which bind to their complementary sequences, Glutathione or derivatives which bind to glutathione transferase (GST). Other pairs that bind specifically such as antigen or hapten which bind to antibody can be used as well. Maltose can be captured by maltose binding proteins. Basically, any pair that can bind each other specifically with sufficient affinity can be used depending on the needs.

In general, any affinity tag-capturing reagent pair commonly used for affinity enrichment which meets the suitability criteria discussed above. Biotin and biotin-based affinity tags are preferred. Of particular interest are structural modified biotins, such as d-iminobiotin, which will elute from avidin or strepavidin columns easily by lowering the pH to below 4. Many methods for biotin and iminobiotin synthesis are known to those skilled in the art and are previously described in patent number: WO97/10854; WO99/42591; RU2102395; WO87/01391; US2001/0016343; U.S. Pat. Nos. 6,242,610; 6,140,507; 5,274,107; 5,247,095; 4,709,044; 4,656,289; 4,636,566; 4,228,295; 4,189,586; 4,130,713; 4,130,712; 4,124,595; 4,054,740; 4,029,647; 3,979,396; 3,978,084; 2,489,236; 2,489,235; 2,466,232; 3,687,967.

Immobilizer—

An immobilizer first criterion is to be chemically inert. The immobilizer or part of it should not participate in any chemical reaction but to serve as an anchor to select labeled molecules away from the rest of the sample. Immobilizers can be small beads such as agarose, sepharose, plastic or other polymers that can be selected by sedimentation or filtering. It can also be specific beads such as para-magnetic beads which can be attracted by a magnetic field for isolation purpose. Other suitable immobilizers include surfaces of reaction vessels whether they are glass, plastic, polymer etc. with additional chemical modifications to enable coupling of linkers and reactive groups.

An immobilizer can be readily linked to a linker connected to a reactive group, or it can be pre-activated by having an activated group used for coupling with the linker to form a strong bond. This bond is preferably a covalent bond but may also be other types of bonds if they are sufficiently strong enough for the purpose of selection. An example of a pre-activated immobilizer is plastic with SH hanging from the surface. The reactive groups also have SH groups so that when put together under oxidizing condition, they form S—S linkage acting as a cleavable linker. Obviously, reactive groups by themselves can also dimerize together with S—S linkage but they can be washed away, subject to reduction to recover the original reagent for reuse. The immobilized SH groups on the immobilizer can't move close together so they are not likely to dimerize. An example of non-covalent pre-activated group is single-stranded DNA which can capture reactive groups linked to a complementary ssDNA.

Reactive Group—

The reactive group can be a chemical group that selectively reacts with certain functional groups on proteins, DNA, lipids, sugars steroids etc. or is a substrate of an enzyme or chemical reaction of interest. This reactive group will react and form a covalent bond with the molecules of interest through specific functional groups or become covalently linked as a result of an enzymatic reaction as occurred in a condensation reaction. Any selectively reactive group should react with a functional group of interest that is present in at least a portion of the molecules of interest in a sample. Reaction of these reactive groups with functional groups on these molecules should occur under conditions that do not lead to substantial degradation of the compounds or target molecules in the sample to be analyzed. Examples of selectively reactive groups suitable for use in the selection reagents of this invention include those that react with sulfurhydryl groups (SH) to tag proteins containing cysteine, those that react with amino groups ($NH_3$), carboxylate groups (COOH), ester groups, phosphate groups, and aldehyde and/or ketone groups or other groups formed after fragmentation with CNBr, homoserine lactone.

Thiol reactive groups include epoxides, α-haloacyl groups, nitriles, sulfonated alkyls or aryl thiols, vinyl pyridines and maleimides. Amino reactive groups tag amino groups in proteins, these include sulfonyl halides, isocyanates, isothiocyanates, active esters, including tetrafluorophenyl esters, and N-hydroxysuccinimidyl esters, acid halides, and acid anhydrides. In addition, amino reactive groups include aldehydes or ketones in the presence or absence of $NaBH_4$ or $NaCNBH_3$.

Carboxylic acid reactive groups include amines or alcohols in the presence of a coupling agent such as dicyclohexyl-carbodiimide, or 2,3,5,6-tetrafluorophenyl trifluoroacetate and in the presence or absence of a coupling catalyst such as 4-dimethylaminopyridine; and transition metal-diamine complexes including Cu (II) phenanthroline Ester reactive groups include amines which, for example, react with homoserine lactone.

Phosphate reactive groups include chelated metal where the metal is, for example Fe (III) or Ga (III), chelated to, for example, nitrilotriacetic acid or iminodiacetic acid.

Aldehyde or ketone reactive groups include amine plus $NaBH_4$ or $NaCNBH_3$, or these reagents after first treating a carbohydrate with periodate to generate an aldehyde or ketone.

Enzymatic substrates such as ATP, S-Adenosyl-L-Methionine, can give up a groups such as phosphate or methyl to label molecules of interest when used with enzymes such as kinase or methylase. Sugars such as mannose can also act as substrate using a glycosylation enzyme to make N-link or O-link glycans. Such glycans are also suitable affinity tags that can be selected by lectin affinity chromatography.

Overall, any reactive groups or substrates that are capable of forming a covalent bond with target molecules with or without the use of an enzyme or additional reagent can be used. The preferred reactive groups usually have certain specificity to allow labeling of one type of molecules such as proteins more favorably over all other types.

Linker, Spacer—

A spacer arm made of several carbons can provide the needed space for the reactive group to freely react with molecules of interest. A linker acting as spacer is sometime necessary between a reactive group and an affinity tag or immobilizer so that the reactive group is not sterically hindered from reacting with molecules of interest. A cleavable linker is optional for affinity tag, but may be necessary for immobilizer when it is coupled to a reactive group. A small enough affinity tag may not interfere with the molecule it labels, thus may remain attached throughout the analysis. However, removing the same molecule from an immobilizer is necessary for most experiment.

A linker can be engineered to be cleavable chemically or physically. A chemically cleavable bond can be cleaved by a chemical reaction, change in pH, or an enzymatic reaction. A physically cleavable bond is one that breaks when some physical change takes place. An example of chemically cleavable linker contain an S—S group so that when reduced by reducing reagent such as 2-mecaptoethanol the bond is cleaved. An example of a physically cleavable bond is one that is light sensitive and can be photo activated to breakup the chemical bond. Yet another example is one that contains a heat-labile bond that fall apart as temperature increase.

The following is a representative list of various cleavable linkers. Photo-cleavable groups in the linker may include the 1-(2 nitrophenyl)-ethyl group. Thermally labile linkers may, for example, be a double-stranded duplex formed from two complementary strands of nucleic acid, or other thermal labile interactions. Cleavable linkers also include those having disulfide bonds, acid or base labile groups, including among others, diarylmethyl or trimethylarylmethyl groups, silyl ethers, carbamates, oxyesters, thioesters, thionoesters, and a-fluorinated amides and esters. Enzyme-cleavable linkers can contain, for example, protease-sensitive amides or esters, P-lactamase-sensitive P-lactam analogs, thrombin cleavage sequence, enterokinase cleavage sequence and linkers that are nuclease-cleavable, or glycosidase-cleavable.

Displacement Ligand

A displacement ligand is optionally used to displace affinity tags from capturing reagent. Suitable displacement ligands should not typically present in samples unless added. These ligands should be chemically and physically stable and their main function is to disrupt the interaction between the affinity tag and the capturing agent. Molecules that are similar to affinity tags can be used as displacement ligands by competitive binding to limited capturing agents. Other types of ligands are those that can cause alteration in capturing agents or affinity tags to disrupt their interactions.

DESCRIPTION OF THE PREFERRED EMBODIMENTS

Labeling Reagents:

There are two important parts in each labeling reagent: a reactive group, and a distinguishable radioactive isotope. The reactive group is one that reacts to and forms a bond with the molecules of interest. The radioactive isotope enables rapid detection and quantification of labels molecules. In addition, a third part—a selection tag—can be added to the labeling reagent to further enhance its usefulness. The selection tag can be an affinity tag or an immobilizer thus allowing labeled molecules to be separated from unlabeled molecules. Pair or trio of labeling reagents can be chemically identical with different radioactive isotopes allow labeling of two or three samples that can be mixed together for co-analysis. After all necessary separations are done, relative quantity of molecules originated from each sample can be compared by comparing radiation signals unique to each radioactive isotope.

Spacer arms or cleavable linkers can also be added between affinity tags or immobilizers and reactive groups. One or more elements on the part of the labeling reagent that will remain with the molecule it labels can easily be replaced with a radioactive isotope. Spacer arms help eliminate steric hindrance allowing reactive groups to freely penetrate molecules of interest. Cleavable linkers allow affinity tags or immobilizers to be removed from labeled proteins leaving minimal modifications on these proteins.

These reagents come in pair or even trio labeled with distinguishable radioactive isotopes such as $^3H$ and $^{14}C$ pair; $^{32}P$ and $^{33}P$ pair; $^{14}C$ and $^{35}S$ pair; $^3H$, $^{14}C$, and $^{35}S$ trio . . . etc. Common organic compounds contain both hydrogen and carbon thus simple substitution of $^3$H or $^{14}$C will do. The labeling tags are thus chemically identical therefore they will behave equally and the identical molecules that are labeled with these tags will also behave equally. A caution when choosing which atom to replace is that atoms that are displaced in the labeling or chemical reaction should not be chosen, but only atoms that remain fairly constant before or after labeling reaction should be used. Hydrogen in the position that can be exchanged away (low pKa) should not be used. Thus atoms that are chosen for radioactive replacement should be those that remain part of the reagent ending up on the molecule to be labeled. These atoms are preferably not participating in any chemical reaction at all.

While being chemically identical, the different labels are distinguishable because their different radioactive isotopes have different properties such as difference in radiation energy, half-life and contributing mass. Scintillation counter can be used to distinguish radiation from isotope with significant difference in radiation energy. Quantifying total radiation before and after a decay period can allow quantifying radiation from a mixture of isotopes with difference in half-life. While the preferred labeling reagents are chemically identical, other reagents that are sufficiently similar can also be used if necessary. When non-identical reagents are used, care should be taken to validate that the pair of reagents can label the same sample equally, and the labeled portions behave equally.

Biotin and imino-biotin are the preferred affinity tag due to their small size and high selection affinity by avidin/strepavidin. For simple labeling where the biotin tag does not have to be removed, it can be linked directly to any chemical reactive group that can react with proteins, lipid, DNA or any other types of molecules of interest for the purpose of carrying out the analysis. The biotin molecule itself can be labeled with radioactive isotope such as $^3$H, $^{14}$C, or $^{35}$S. The chemical reactive group can contain $^3$H, $^{14}$C, $^{35}$S, $^{32}$P, $^{33}$P, or other radioactive isotopes for the purpose of distinguishable quantification while the isotope is used in a mixture with another radioactive isotope.

When a cleavable linker is used with a biotin tag, it is not necessary for the biotin group to carry any radioactive label. However, it is essential for the chemical reactive group and the remaining part of the linker to have the radioactive isotope label. Most chemical reactive groups must have hydrogen or carbon as their components, thus these can be replaced with $^3$H or $^{14}$C. The hydrogen or carbon selected for replacement must be the one remaining with the molecule of interest. A cleavable disulfide linker can have a $^{35}$S as the remaining sulfur while the other S, the rest of the linker, and the biotin group that will be detached from the chemical reactive group after cleavage does not have to contain isotope label.

An immobilizer such as beads or sturdy surface and reaction vessel can be used for coupling of labeling reagent. The sample to be labeled can be mixed with the beads or added to the reaction vessel and allowed to react. Then un-reacted molecules are washed away before the cleavable linkage is cleaved to release labeled molecules. These molecules are now ready to be mixed together for simultaneous analysis.

Methods of Analysis:
Label two samples with a pair of chemically identical reagent containing different radioactive isotope.
Mix two samples together as soon as possible
Select labeled molecules away from unlabeled molecules using the affinity tags or immobilizers.
Displace affinity tags capturing agents or cleave off immobilizers.
Subject the protein mixtures to any means of separation into a plurality of fractions.
Quantify unique each radioactive isotope utilizing their difference in radiation energy or half-life as discriminator.
Pan for fractions with deviated isotope ratio
Identify the differentially abundant proteins or peptides by mass spectrometry or other methods. Note that the different isotopes may also cause a mass difference that can be used for double checking the result here.

Because the method of detection is so sensitive, an aliquot of each fraction after one separation can be used for radioactive ratio analysis and then the fraction can be further separated if desirable. A good outline of this process is described in Example 1 below.

Proteins in two samples are labeled with a pair of selective labeling reagents which are chemically identical and containing different radioactive isotopes. After labeling reactions are completed, both samples are mixed together as soon as that is possible and then labeled proteins are selected away from unlabeled proteins. Any cleavable linkers are now cleaved to release the labeled proteins, or affinity tags are eluted of their capturing agents. The protein mixture can be subjected to any means of fractionation such as chromatography, electrophoresis, immunoprecipitation, immunomagnetic capturing, array profiling, differential extraction or precipitation such as salt-cut precipitation or organic solvent extraction or precipitation, heat-treatment precipitation, microfluidic device, capillary electrophoresis, differential centrifugation, or gradient separation . . . etc. After separation, the fractions are subjected to scintillation counting or other equivalent methods to determine the ratio of different radioactive isotopes in each fraction. Fractions with aberrant ratio are those with differentially abundant proteins. Other fractions can be discarded or further separated depending on their content.

Types of Analyses:

The most popular use of this invention is for proteomic analysis where two samples of proteins are assayed to pan for differentially abundant proteins as biomarkers. Such biomarkers can be used for many applications from disease diagnostic to drug discovery and development. While protein is the major focus, other molecules can also be compared to pan for differentially abundant molecules just as proteins.

The invention can also be used to study posttranslational events such as phosphorylation, glycosylation . . . etc. if the labels are modified slightly. One way to compare these post translational events is to select the modified proteins away from unmodified proteins by known means such as metal ion chelating affinity column for phosphate groups and lectin affinity column for sugar groups. The modified or the unmodified population of proteins or both can be labeled for simultaneous co-analysis to pan for differentially abundant modified proteins vs. unmodified proteins.

Another way to compare posttranslational modification events is by using labels that can differentially label modified vs. unmodified proteins. For instance, phosphate groups can only be added to unphosphorylated serines, tyrosines, and threonines. Such phosphate groups can contain $^{32}$P or $^{33}$P to enable mixing and co-analysis for reliable quantitative comparison. Phosphate groups attached to a linker and a selection tag is also possible.

EXAMPLES

Example 1

Biomarker Discovery Process Using Two Biological Samples:

Equal amount of blood plasma sample from a person when he is healthy and when he is sick are used to pan for protein changes in the plasma proteome as a result of the ailment. The objective is to discover proteomic changes associated with the ailment. One plasma sample is labeled with a cleavable biotin labeling reagent (reactive group-SS-biotin) containing tritium, while the other sample is labeled with a chemically identical reagent containing carbon-14. Both samples are then combined and allowed to bind to strepavidin-sepharose (packed as an affinity selection column). The column is then washed with various buffers to remove unlabeled molecules and other non-specific interactions. Then buffer containing reducing reagent dithiothreitol is used to reduce (cleave) the SS bond. This cleavage releases the labeled molecules from the column for use in analysis. One population of this molecule will contain $^3$H-tag while the other population will contain $^{14}$C-tag. These tags are chemically identical thus they will hardly be differentiated by many methods of fractionation, gel electrophoresis etc. After fractionation, each fraction can be examined by counting $^3$H/$^{14}$C ratio to identify fractions with ratio deviation. Select fractions will be further examined to determine the exact molecules causing the imbalance. These are the molecules that are differentially abundant between the two test samples as a result of the diseased condition.

A good method for fractionation is tandem chromatography. The mixture is first fractionated by one form of chromatography, and then aliquots from fractions are examined by counting on scintillation counters for $^3$H/$^{14}$C isotope ratio. The isotope ratio count of an aliquot from the original mixture will be used in conjunction with the count of most fractions to establish a "norm" indicating equal amount of proteins from both samples. The possible outcomes of scintillation counting are:

1. Isotopes' ratio is within established norm and high total radioactivity count (implies that a lot of proteins are present): These fractions have approximately equal amount of proteins amount from both samples. These samples are destined for further separations by a different type of chromatography or gel electrophoresis.
2. Isotopes' ratio deviates from established norm and high total radioactivity count: These are the samples containing potential biomarkers. These fractions can be analyzed on SDS-PAGE to determine if the protein(s) with variation in abundance can be isolated as a band for identification by mass spectrometry. Note should be made regarding whether $^3$H or $^{14}$C labeled sample has more proteins.
3. Isotopes' ratio is within established norm and low total radioactivity count: These fractions have little amount of proteins which are equally contributed by both samples. These can be discarded if there are deemed to be too few proteins to pursue further separation.
4. Isotopes' ratio deviate from established norm and low total radioactivity count: These fractions can be stored for direct identification by mass spectrometry or other methods without any further separation. Additionally, these fractions may need to be concentrated if necessary.
5. Low to no count: These are the fractions without significant amount of proteins such as fractions of flow-through and void volume etc. . . . Naturally, these fractions will be discarded.

Continuing fractionation will ultimately yield all the molecules whose level of abundance varies between the two test samples. This method is superior to conventional method of analysis because it allows both multiplexing and rapid detection. Without multiplexing, tandem multidimensional chromatography is normally not possible to process two samples and reproduce identical fractions with sequential or parallel runs. The use of radioactive isotopes enables rapid detection and quantitative comparison make this method superior to labeling with ICAT reagents and analyzing each fraction by mass spectrometry. Obviously, this method is much more efficient because one does not have to process every fraction by mass spectrometry, analyze the complex mass spectra to identify just a few fractions with the desirable biomarkers.

Example 2

Comparative Analysis of Three Samples

Biological samples from a patient treated with a know drug, a placebo and an experimental drugs are used for protein profiling comparison in this experiment. All samples are labeled with radioactive imino-biotin labeling reagent. One sample is labeled with $^3$H, another with $^{14}$C, and another with $^{35}$S. All three samples are mixed together and affinity select by strepavidin column. After unbound molecules are washed away, bound molecules are eluted with buffer having pH less than 4. These molecules are neutralized, non-specific proteins may be added, and then bind to a protein array. Washing and further non-specific competition removes non-specific bindings. Radiation signals from the array are quantified to determine $^3$H signals, then quantification before and after a decay period determine $^{35}$S signal and calculation yield $^{14}$C as remaining signals. The protein pattern of changes due to known drug treatment and experimental drug treatment can be compared with placebo treatment for efficacy study.

Example 3

Alternative Approach to Identifying Differentially Abundant Proteins Between Samples.

A person's biological sample is taken when he is healthy and labeled with selective labeling reagent containing a long-live radioactive isotope such as $^{14}$C. Labeled molecules are stored in aliquots for used in later assays. These labeled molecules are tested for competitive binding with the same unlabeled sample by binding to a protein array to ensure that labeled and unlabeled molecules can compete and bind fairly equally. For instance, using enough proteins to saturate all spots on the protein array, a 50/50 mixture of labeled sample and unlabeled sample should yield 50% signals for all spots compared to just 100% labeled sample alone.

When the person is sick, the same type of biological sample can be taken and mixed with labeled sample taken when healthy and profiled on a protein array. Theoretically, equal amount of unlabeled proteins and labeled protein will reduce the signal read equally; however the patient condition causes some proteins to become more abundant while others become less abundant. Some proteins are known to stay constant regardless (known as housekeeping proteins), these are used as benchmark to determine which proteins are differentially abundant between sick and healthy state. The percentage of signal for spots capturing housekeeping proteins is used to determine if other captured proteins are equally balanced between samples. Those that are imbalanced can be identified and used to develop or make the diagnosis.

Example 4

Post-translational Studies

Two samples of proteins are labeled with different radioactive selection reagents, mixed together and then selected for labeled proteins. Phosphorylated proteins are separated by metal-ions affinity columns, while glycosylated proteins are selected for by lectin affinity columns. These different groups of proteins are further separated to identify differentially abundant proteins within each group. This analysis yields differentially abundant proteins with certain post-translational modifications. When comparing modified proteins and unmodified proteins, deduction can be made if certain proteins are differentially modified.

Example 5

Affinity Labeling for Glycosylation Studies

Proteins from two samples to be compared are glycosylated with mannose labeled with $^3H$ for one sample and $^{14}C$ for the other sample. Then both samples are combined and the proteins affinity selected by lectin affinity columns. These proteins are then separated by other methods to pan for differentially labeled proteins. This method has an advantage over the method described in example 4 in that it can quantitatively compare the degree of glycosylation in each particular protein, not just the relative abundant of a form of glycosylated protein.

Example 6

Differentially Interacting Protein Studies

The labeling method of this invention is also affected by protein differential folding and differential interaction with ligands and other macromolecules especially when the labeling method does not disrupt these native interactions. Using this quality, the method can also be used to isolate proteins that are differentially labeled as a result of these differential interactions or differential foldings.

Ligand-dependent protein interaction is the subject of this study. Protein lysate from cultured cells are divided into equal portions into which ligands or vehicles (delivery solvent) are added. Then the different portions are labeled with labeling reagents containing different radioactive isotopes in pair or trio and then combined for co-analysis. The protein mixtures are separated into fractions by various methods as described in previous examples. The fractions are examined for isotope ratio to look for fractions with ratio deviation. The deviation is due to differentially labeling of proteins between the samples. Further analyses including mass spectrometry and decoding isotope labeling can also map the interaction sites.

Example 7

Comparing the Degree of DNA Methylation between Two Sources of DNA

DNA from two populations of cells is compared for the purpose of discovering any difference in methylation of certain genes that can later be used as biomarkers. For instance, two set of DNA isolated from B cells from a lymphoma patient at different stage of disease progression or treatment can be compared. Equal amount of exogenous DNA is added to each sample. This DNA is synthesized to contain various percentages of methylated bases and non-methylated sites. The DNA samples are treated separately with methyl transferase using $^3H$ labeled methyl groups for one set and $^{14}C$ labeled methyl groups for the other set from the universal methyl donor S-Adenosyl-Methionine. Certain empty methylation sites on both DNA are methylated with labeled methyl groups. The DNA are cleaned from methylating reagent and mixed together. The mixture is subjected to restriction enzyme digestion and then profiled on a DNA array. Signal from $^3H$ and $^{14}C$ are differentially detected by first exposing directly to a phosphor-imaging screen and then exposing to the same screen but with a thin blocking screen for the same amount of time. Spots capturing exogenous DNA are used as reference standard to determine relative isotope ratio representing equal amount of methylation in both samples. These spots can also control for methylation efficiency. The best way to determine isotopes' quantity and ratio is to have an array of these mixtures at different quantity and ratio quantified and stored by the same instrument as reference scale for calculation.

Further Clarifications:

The above examples are only representation of possible uses of this invention and should not be interpreted as an exhaustive list. Many variations are possible by changing the labeling reagents to label specific groups, specific modifications on a molecules, or specific sites due to accessibility . . . etc. These variations are understood by those skilled in the art. It should be apparent that the method of this invention is the coding of at least two samples with two different radioactive isotopes for combined analysis. In addition, a means for substantially isolating labeled molecules from unlabeled molecules is the further improvement over the parent patent application.

While the preferred pair or trio of labeling reagents are chemically identical bearing different radioactive isotopes, substantially similar reagents can also be used. The main judgment for similarity is depending on the purpose of use. For procedures where the structure of target molecules to be labeled is important, then structural similarity is the most desirable attribute. For procedures where the reactivity of target molecules is important, then substantial similarity in resulting chemical functional groups in the labeled molecules is the most important attribute. Similarity is a quality that can be determined readily by those skilled in the art, and can also be confirmed empirically by a validation experiment. For instance, splitting a sample into portions to be labeled by similar labeling reagents for combined analysis should yield results indicating that the portions contain the same content for the reagent to pass the similarity test for that particular assay or experimental setup.

The methods of selectively quantifying radioactive isotopes are described in the parent patent application U.S. Ser. No. 10/680,277 and related international patent application serial number PCT/US 04/02442, the content of both these applications are incorporated herein as reference. Briefly, different radioactive isotopes emit different energy of the same or different types of radiation. Scintillation counting using recent model scintillation counters can differentially quantify different radioactive isotopes in a mixture especially $^{14}C$ and $^3H$. Additionally, a user can also make a set of standard mixture to create reference readings of known ratio of isotopes at various dilutions to enable better quantification by comparison. Radioactive isotopes also have different half-lives, thus they will decay at different rate. Using the known half-lives of radioactive isotopes in the mixture, a user can quantify total radiation before and after a decay period and use that information to determine the relative amount of radiation belonging to each radioactive isotope. Different radioactive isotopes can also contribute different mass to a chemically identical reagent. For instance, a methyl group containing $^{14}C$ is 2 atomic mass units (amu) heavier than a normal methyl group and is 4 amu lighter than a methyl group containing 3 atoms of $^3H$. Such mass differences can be deciphered using existing mass spectrometry.

I claim:

1. A method of panning for at least one molecule of interest from two samples comprising the steps of:
    a) labeling test molecules in a first sample with a first labeling reagent containing a first radioactive isotope;
    b) labeling test molecules in a second sample with a second labeling reagent containing a second radioactive isotope;
    c) mixing said first sample and said second sample into a mixture for simultaneous panning;
    d) separating said mixture into fractions or groups of molecules;
    e) using the difference in radiation energy between said first radioactive isotope and said second radioactive isotope to determine an isotope ratio for each group of molecules;
    f) comparing the isotope ratios among said groups of molecules; and,
    g) selecting at least one group of molecules with deviated isotope ratio to look for the molecule of interest.

2. The method of claim 1 wherein said molecule of interest is differentially abundant between said first sample and said second sample.

3. The method of claim 1 wherein said molecule of interest is differentially modified in said first sample versus in said second sample.

4. The method of claim 1 wherein said molecule of interest is differentially folded in said first sample versus in said second sample.

5. The method of claim 1 wherein said molecule of interest is differentially interacting with at least one other molecule in said first sample versus in said second sample.

6. The method of claim 1 wherein said molecule of interest is differentially labeled degraded in said first sample versus in said second sample.

7. The method of claim 1 wherein said molecule of interest is differentially interacting with at least one other molecule resulting in differential labeling in said first sample versus in said second sample.

8. The method of claim 1 further comprising a step of substantially selecting labeled molecules away from unlabeled molecules.

9. The method of claim 1 wherein said molecules of interest is a protein.

10. The method of claim 1 wherein said first labeling reagent is structurally identical to said second labeling reagent.

11. The method of claim 1 wherein said first labeling reagent is chemically identical to said second labeling reagent.

12. The method of claim 1 wherein said first labeling reagent and said second labeling reagent further comprise a means for substantially selecting labeled molecules away from unlabeled molecules.

13. The method of claim 1 further comprising a step of identifying said molecule of interest.

14. A method of panning for at least one molecule of interest from two samples comprising the steps of:
    a) labeling test molecules in a first sample with a first labeling reagent containing a first radioactive isotope;
    b) labeling test molecules in a second sample with a second labeling reagent containing a second radioactive isotope;
    c) mixing said first sample and said second sample into a mixture for simultaneous panning;
    d) separating said mixture into fractions or groups of molecules;
    e) determining an isotope ratio for each group of molecules;
    f) comparing the isotope ratios among said groups of molecules;
    g) selecting at least one group of molecules with deviated isotope ratio to look for the molecule of interest;
    h) separating at least one group of molecules with normal isotope ratio into smaller groups of molecules or subfractions to further reduce the amount of unique molecules in each subfraction;
    i) comparing isotope ratio between said subfractions; and,
    j) selecting at least one subfraction with deviated isotope ratio to look for additional molecule of interest.

15. The method of claim 14 further comprising a step of identifying said additional molecule of interest.

16. A method of panning for at least one molecule of interest from two samples comprising the steps of:
    a) labeling test molecules in a first sample with a first labeling reagent containing a first radioactive isotope;
    b) labeling test molecules in a second sample with a second labeling reagent containing a second radioactive isotope;
    c) mixing said first sample and said second sample into a mixture for simultaneous panning;
    d) separating said mixture into fractions or groups of molecules;
    e) using the difference in half-life between said first radioactive isotope and said second radioactive isotope as a means to determine an isotope ratio for each group of molecules;
    f) comparing the isotope ratios among said groups of molecules; and,
    g) selecting at least one group of molecules with deviated isotope ratio to look for the molecule of interest.

17. The method of claim 16 further comprising a step of identifying said molecule of interest.

* * * * *